(12) United States Patent
Buckley

(10) Patent No.: US 10,821,254 B2
(45) Date of Patent: Nov. 3, 2020

(54) RESPIRATORY CONNECTOR

(71) Applicant: Intersurgical AG, Vaduz (LI)

(72) Inventor: Daniel John Buckley, Hampshire (GB)

(73) Assignee: Intersurgical AG, Vaduz (LI)

( * ) Notice: Subject to any disclaimer, the term of this patent is extended or adjusted under 35 U.S.C. 154(b) by 909 days.

(21) Appl. No.: 15/321,584

(22) PCT Filed: Jun. 23, 2015

(86) PCT No.: PCT/EP2015/064088
§ 371 (c)(1),
(2) Date: Dec. 22, 2016

(87) PCT Pub. No.: WO2015/197605
PCT Pub. Date: Dec. 30, 2015

(65) Prior Publication Data
US 2017/0157355 A1   Jun. 8, 2017

(30) Foreign Application Priority Data

Jun. 25, 2014 (GB) .................................. 1411288.2

(51) Int. Cl.
*A61M 16/08* (2006.01)
*A61M 39/10* (2006.01)
*A61M 16/00* (2006.01)

(52) U.S. Cl.
CPC .... *A61M 16/0816* (2013.01); *A61M 16/0875* (2013.01); *A61M 39/105* (2013.01); *A61M 2016/003* (2013.01); *A61M 2039/1027* (2013.01); *A61M 2039/1077* (2013.01); *A61M 2039/1083* (2013.01); *A61M 2039/1088* (2013.01)

(58) Field of Classification Search
CPC ............ A61M 39/105; A61M 16/0816; A61M 16/0875; A61M 16/0841; A61M 2039/1027; F16L 37/56
See application file for complete search history.

(56) References Cited

U.S. PATENT DOCUMENTS

| 4,859,859 A | * | 8/1989 | Knodle | ................ A61B 5/0836 250/504 R |
| 5,201,552 A | * | 4/1993 | Hohmann | ............. F16L 33/213 285/120.1 |
| 5,709,665 A | | 1/1998 | Vergano et al. | |
| 5,860,677 A | * | 1/1999 | Martins | ................. F16L 37/088 285/26 |

(Continued)

FOREIGN PATENT DOCUMENTS

| EP | 2317200 A1 | 5/2011 |
| EP | 2497515 A1 | 9/2012 |

(Continued)

*Primary Examiner* — Timothy A Stanis
(74) *Attorney, Agent, or Firm* — Young Basile Hanlon & MacFarlane, P.C.

(57) ABSTRACT

A respiratory connector is provided for connecting corresponding ends of a plurality of gas flow lines to a corresponding plurality of ports. The connector comprises first and second connector formations, and a bridge extending between the first and second connector formations. The bridge is actuable to allow a spacing between the first and second connector formations to be varied during use.

17 Claims, 2 Drawing Sheets

(56) References Cited

U.S. PATENT DOCUMENTS

| | | | |
|---|---|---|---|
| 2007/0277824 A1* | 12/2007 | Aylsworth | A61M 16/0666 128/204.23 |
| 2008/0221470 A1 | 9/2008 | Sather et al. | |
| 2010/0269828 A1 | 10/2010 | Orr et al. | |
| 2011/0204622 A1* | 8/2011 | Lewis | F16L 37/0841 285/313 |
| 2012/0191029 A1 | 7/2012 | Hopf et al. | |
| 2013/0092247 A1* | 4/2013 | Lee | A61M 1/0064 137/15.01 |
| 2014/0238397 A1 | 8/2014 | Buechi et al. | |
| 2014/0311578 A1* | 10/2014 | Veneroni | A61M 39/105 137/1 |
| 2014/0358022 A1* | 12/2014 | Sansom | A61M 16/0816 600/537 |

FOREIGN PATENT DOCUMENTS

| | | |
|---|---|---|
| WO | 2011079226 A1 | 6/2011 |
| WO | 2013045563 A1 | 4/2013 |

\* cited by examiner

RESPIRATORY CONNECTOR

CROSS REFERENCE TO RELATED APPLICATION

The present application claims priority to Great Britain Patent Application No. 1411288.2, filed Jun. 25, 2014, incorporated herein in its entirety.

TECHNICAL FIELD

The present invention relates to connectors for respiratory systems and more particularly to respiratory gas flow connectors.

BACKGROUND

Patient respiratory systems allow the delivery of respiratory gases from a gas/pressure source to a patient interface and may be used for a number of purposes, including oxygen or anaesthesia delivery and/or ventilation of patient. A plurality of tubes and accompanying devices may be provided in a flow path from the gas source to the patient interface. It is known within existing patient respiratory systems to provide means for monitoring flow, typically expiratory flow, in order to assess the state of the patient and/or respiratory gas delivery system.

A monitoring device requires a gas flow connection to the relevant point within the respiratory system in order to be able to measure the flow parameters under assessment. For example, in order to be able to measure flow rate, it is known to monitor pressure on opposing, i.e. upstream and downstream, sides of a flow restriction within the respiratory system. Accordingly, there is a need to provide a number of flow connections between the flow path of the respiratory system and a monitoring device.

The management of the resulting plurality of flow connections, and the associated tubing can cause problems for a carer or operator of the monitoring device. Given the critical nature of the relevant respiratory monitoring connections, it is known to provide different monitoring tubes with different tube connectors so as to avoid the possibility of the multiple tubes being connected incorrectly. However, the provision of multiple separate and distinct tubes can result in a carer being required to undergo a trial and error process to ascertain which tube end connector fits the relevant port. Furthermore, conventional arrangements do not provide in themselves positive verification that all the relevant tubes have been correctly connected at the time of connection. For example, it is possible that a carer in a busy environment could correctly connect the opposing ends of one tube end but forget to connect both ends of one or more further or associated tube.

Conventional monitoring apparatus may also have different monitoring port locations such that it is difficult to provide a single, common connecting tube arrangement that can accommodate the different port arrangements whilst also being simple to manage.

Whilst the above problems are described in relation to patient respiratory systems, similar problems may occur when attempting to monitor respiratory function in other scenarios, for example when monitoring expiratory flow parameters in applications in which patient therapy is not required (e.g. monitoring lung or respiratory function in order to determine fitness or wellbeing for a user).

SUMMARY

It is an aim of the present invention to provide a respiratory gas flow connector product which mitigates or resolves one or more of the above described problems.

According to the present invention, there is provided a respiratory connector for connecting a plurality of gas flow lines to a corresponding plurality of ports in use, the connector comprising: a first connector formation comprising a first inlet opening, a first outlet opening and a first internal passage extending there-between; a second connector formation comprising a second inlet opening, a second outlet opening and a second internal passage extending there-between; and a bridge extending between the first and second connector formations, wherein the bridge is deformable to allow a spacing between the first and second connector formations to be varied in use.

A plurality of gas flow lines, comprising first and second flow lines, may be connectable or connected to said respective first and second connector formations. Respective ends of the first and second flow lines may terminate at the first and second connectors and may be fixed thereto, for example by way of adhesive. The end of the first and/or second flow line may or may not be received at the respective first and/or second inlet. The end of the first and/or second flow line may be received within the respective first and/or second connector, for example within the internal dimension of the inlet and/or internal passage.

The invention allows management of a plurality of flow lines by a common connector whilst permitting the required plurality of connections to be made, for example with ports of varying spacing. For example, a common connector design according to the invention can be used to connect to a plurality of different makes/models of machine, for which the port spacing may vary.

The connector may take the form of a connector head.

The bridge may or may not be resiliently deformable. The bridge may or may not comprise a resiliently deformable material. The bridge may comprise a hinge, such as for example a living hinge.

The bridge may or may not be arched, bowed or angled (e.g. chevron-shaped) in form. The first and second connector formations may be spaced in a first direction and at least a portion of the bridge may be obliquely angled relative to the first direction. The bridge may comprise first and second bridge portions depending from the respective first and second connector formations. The first and second bridge portions may be obliquely angled relative to the first direction, for example in opposing senses.

The first and second bridge portions may meet at a corner, e.g. a rounded corner. An interior angle formed between the first and second bridge portions may be an acute angle. The bridge may be arranged such that the spacing between the first and second connector formations, e.g. when the bridge is undeformed, is a maximum spacing. The spacing may be adjusted by pressing the first and second connector formations together, e.g. against a resilience of the bridge.

The bridge may take the form of a web or wall between the first and second connector formations. The bridge may be formed, e.g. moulded, in the desired shape.

The bridge may comprise a polymer material.

The wall thickness of the bridge may be less than the internal dimension of the first and/or second internal passage (e.g. the passage width or diameter). The bridge wall thickness may be between 0.5 and 2 or 3 mm, such as approximately 1 mm.

The first and second connector formations and the bridge may comprise or, be formed of, a common material, for example as a common or unitary body. The first and second connector formations and the bridge may be co-formed, for example by moulding.

The bridge may extend substantially the full length of the first and/or second connector formation, for example in a length direction between the corresponding inlet and outlet openings.

The first and second internal passages may be substantially parallel and/or linear in form. The first and second connector formations may be substantially parallel.

One of the inlet and outlet for each connector formation may be adapted to connect to an associated port. Said one of the first inlet and outlet may have a different form to said one of the second inlet and outlet. The respective forms may differ in internal/external dimensions, such as a diameter/width dimension. The other of the inlet and outlet for each connector formation may be adapted to receive a flow line and may be of the same form and/or internal dimensions.

The first connector formation may be a simple female connector, e.g. having an opening arranged to receive a male spigot formation in which the port is provided.

The second connector formation may comprise inner and outer concentric walls. The connector ends of the first and second connector formations may be provided at the respective outlet opening.

The difference in form between the first and second connector formations ensures that said connections cannot be made with the wrong ports.

According to a second aspect of the invention, there is provided a respiratory tubing product comprising the connector of the first aspect and first and second flow lines depending from the first and second connector formations.

The first and second flow lines may be coupled or connected, e.g. in a side-by-side arrangement, along a portion, such as a majority, of their length. The first and second flow lines may separate a short distance from their respective ends which depend from the connector.

The respiratory tubing product may comprise a third flow line. The third flow line may have a third connector formation, which may be independent of the connector for the first and second flow lines. The third flow line may be coupled or connected to the first and second flow lines, e.g. in a side-by-side arrangement, along a portion, such as a majority, of its length. The third connector formation may be provided at a free end of the third flow line.

The first and second flow lines may be for measuring gas flow. The third flow line may be for measuring the components of the flow.

The connector may comprise a first or distal connector at first or distal end of the first and second flow lines. The respiratory tubing product may comprise a second or proximal connector at the second or proximal ends of the first and second flow lines. The second connector may comprise internal passages for connection of the first and second flow lines to further respective ports. The internal passages of the second connector may be of fixed spacing. The internal passages of the second connector may turn through an angle, such as approximately 90. The second connector may comprise a solid, unitary body in which the internal passages are formed.

The third flow line may comprise a fourth connector formation at its second or proximal end, which may be independent of the second connector.

The product may comprise a spirometry tubing product, for example for attachment between a respiratory gases passage and monitoring means.

A respiratory gases passage member may be provided with the respiratory tubing product, for example as a kit. The respiratory passage member may comprise a main gas path and ports opening into said main gas path for communication with the first and second flow lines. The ports may be spaced by a restriction or flow obstruction within the main gas path. The respiratory passage member may comprise a further port for communication with the third flow line. The passage member may comprise a spirometry adapter.

Any of the preferable features defined in relation to any one aspect may be applied to any further aspect of the invention.

DETAILED DESCRIPTION OF THE DRAWINGS

Practicable embodiments of the invention will be described in further detail below with reference to the accompanying drawings, of which:

DETAILED DESCRIPTION OF THE EMBODIMENTS

Figure 1:
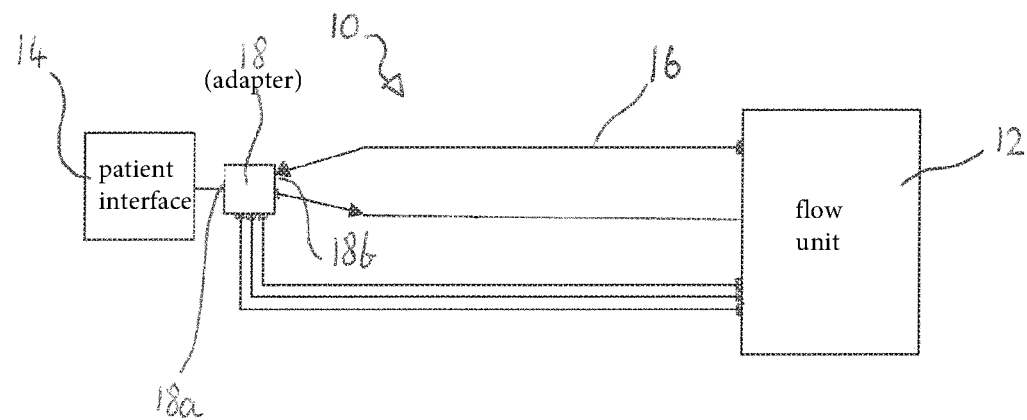
FIG. 1 is a schematic of a patient respiratory system.

Turning firstly to FIG. 1, there is shown an example of a respiratory system 10 in which the invention may be used. The respiratory system 10 comprises in brief a flow control unit or source 12 for supplying respiratory gases to a patient interface 14, which may comprise any conventional type of invasive or non-invasive patient respiratory interface such as a face mask, nasal mask or laryngeal mask airway. A simple example is shown in FIG. 1 in which a simple flow line or tube 16 delivers gases from the flow unit 12 to the interface, although it will be appreciated by the skilled person that one or more intermediary devices, such as humidifiers, heaters and/or sensors could be provided within the respiratory system.

A gas passage adapter 18 is provided at or adjacent the patient interface 14 in order to allow monitoring of the flow mechanics, e.g. by measuring gas flow rates, volumes and/or pressures, as well as the constituents of the gas flow itself, i.e. to perform analysis of the gases therein. The adapter 18 may be connected directly to the interface 14 or spaced therefrom by a short length of tubing. The adapter 18 has main flow openings 18*a* and 18*b* and a plurality of openings or ports therebetween which are used for the spirometry purposes disclosed herein.

In this example, the adapter has first and second ports, which are used for flow mechanics monitoring and a third port which is used for gas sampling/analysis. The first and second ports are spaced by a flow obstruction and may face in opposing directions with respect to the gas flow through the adapter so as to allow determination of a pressure differential between the two ports. The first and second ports may open into the middle of the flow passage within the adapter 18 and may face the opposing ends 18a, 18b. The third opening may be a side opening, e.g. in a side wall of the adapter.

Figure 2:
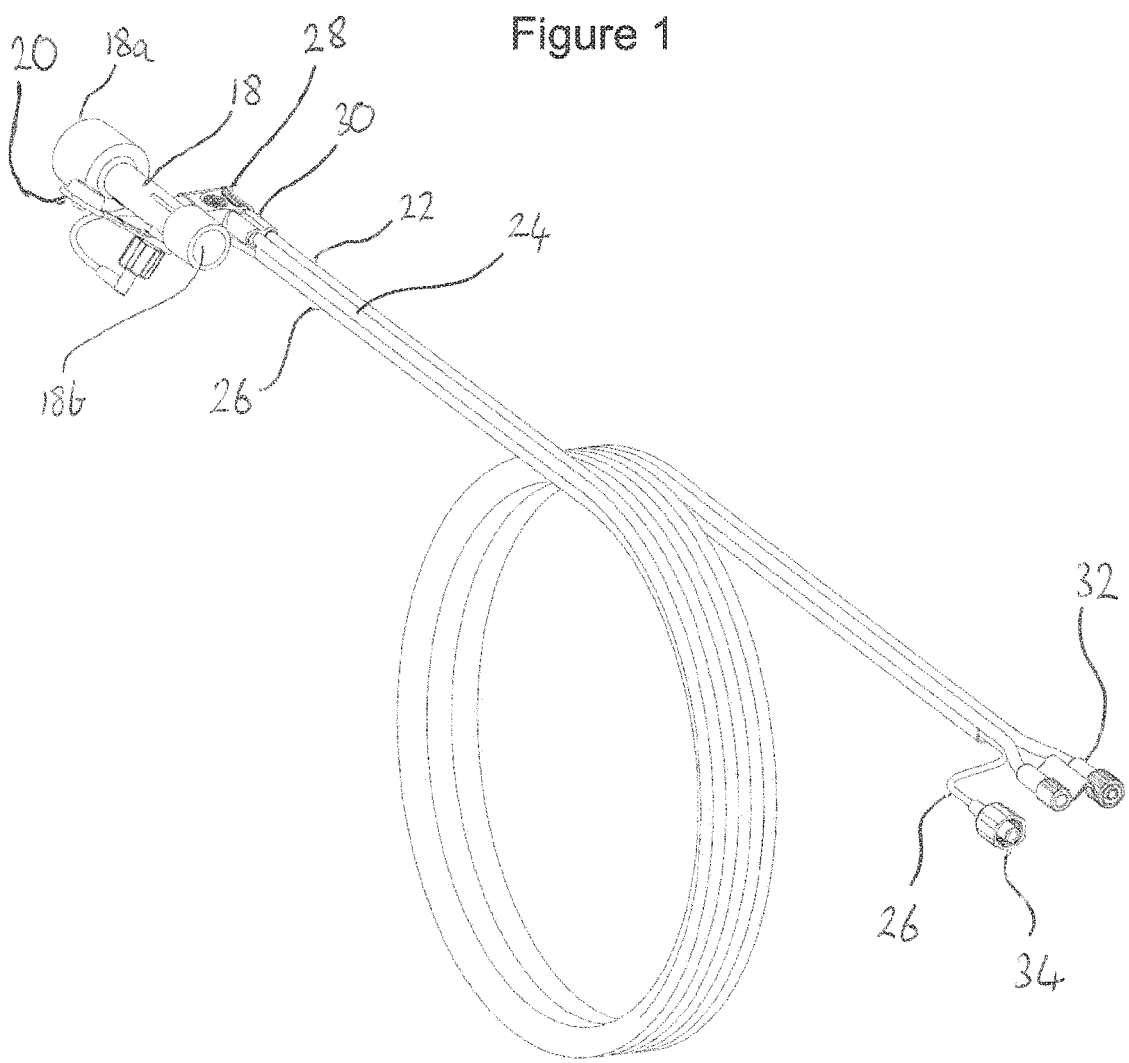
FIG. 2 is a three dimensional-view of a respiratory tubing product comprising a connector according to the invention.

Although covered in FIG. 2, each of the first, second and third ports in the adapter 18 typically have an upstanding spigot formation associated therewith which depends outwardly from the adapter body. In this example, the first and second ports/spigots are aligned in a longitudinal direction along the adapter body and the third port is spaced, e.g. angularly spaced, therefrom. The third port is provided with a port cap 20 as shown in FIG. 2 such that it can be selectively closed if not in use. Accordingly, the adapter may be used to facilitate measurement of flow mechanics only or both flow mechanics and also gas analysis. The measurement of flow mechanics allows monitoring of lung function or mechanical ventilations.

The system of FIG. 1 and the associated spirometry apparatus of FIGS. 2-5 may be used in a respiratory system in which the patient breathes spontaneously or else for mechanical ventilation purposes. As will be understood by the skilled person, the flow control unit 12 may both regulate/drive the flow of gas to the patient and also measure the flow parameters described herein for spirometry purposes. The flow control unit 12 may comprise a conventional respiratory control machine such as an anaesthesia machine, ventilator or similar.

Whilst specific examples of patient equipment are described above, it is to be noted that the flow line connector of the invention may be used in other scenarios in which a plurality of respiratory flow lines require connection to corresponding ports for respiratory flow or function monitoring.

Figure 3:
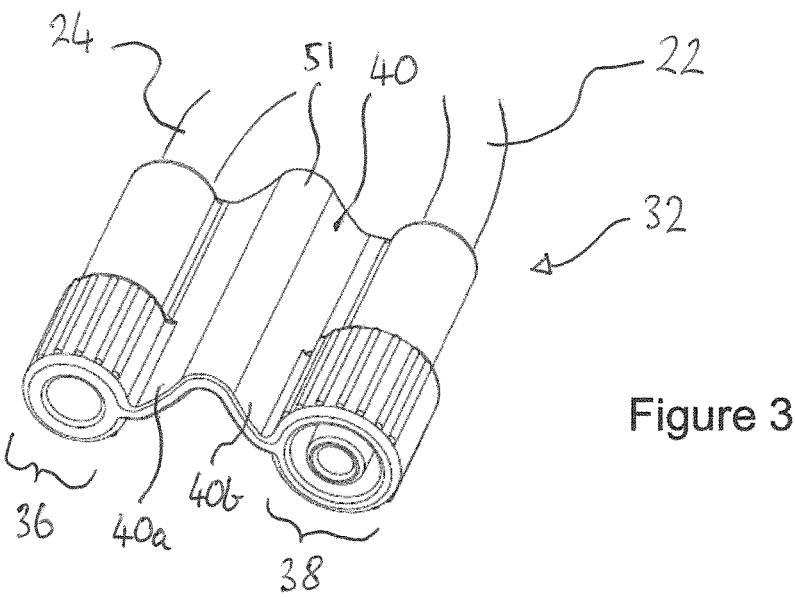
FIG. 3 is a three dimensional view of the respiratory connector of FIG. 2.

Turning now to FIGS. 2 and 3, there is shown an example of the respiratory tubing product and associated connectors in accordance with an example of the invention. The tubing product comprises an array of three individual flow lines 22, 24 and 26, each of which takes the form of a flexible polymer tube. The flow lines 22 and 24 correspond to the first and second flow lines discussed above and the line 26 corresponds to the third flow line. The diameter of the first and second flow lines is typically the same but the third flow line may be narrower.

The flow lines 22-26 are attached together along a majority of their length so as to form a bundle of flow lines which is easy to manage. At the ends which are proximal to the adapter 18, the flow lines 22 and 24 are received in a connector body 28. The proximal ends of the flow lines 22, 24 are received within female connector formations 30 so as to form a close fit therewith. Male connector spigots may be used in other embodiments. The ends of flow lines 22, 24 are typically held in place by an adhesive, such as a glue.

The connector body 28 has two openings adapted to connect with the two respective flow monitoring ports on the adapter 18. The connector body is formed as a unitary moulded body of a polymer material with the necessary openings and internal flow passages formed therein to allow the flow lines to be in independent fluid communication with its respective flow monitoring port. The connector body 28 is provided in the form of an elbow connector such that the internal passages each turn through an angle, such as approximately 90°, between the opposing ends thereof.

Each of the flow lines 22-26 are elongate in form and typically of length of in the region of or greater than 1 m, such as, for example, 2 or 3 m in length.

A connector 32 in accordance with the present invention is provided at the opposing/distal ends of flow lines 22, 24 as shown in FIG. 2 for connection to the associated monitoring ports on the flow monitoring device 12. Monitoring ports on conventional devices of this kind comprise a pair of upstanding male spigots to which the connector 32 will attach in use.

It can be seen that the flow lines 22 and 24 diverge a short distance from the connector 32. The flow line 26 also diverges from the other flow lines at a distance from its distal end, at which a separate connector 34 is provided, which may be a conventional respiratory tube end connector. Thus the connector 34 has a limited freedom of movement relative to connector 32 according to the free length of flow line 26 towards its distal end.

Figure 5:
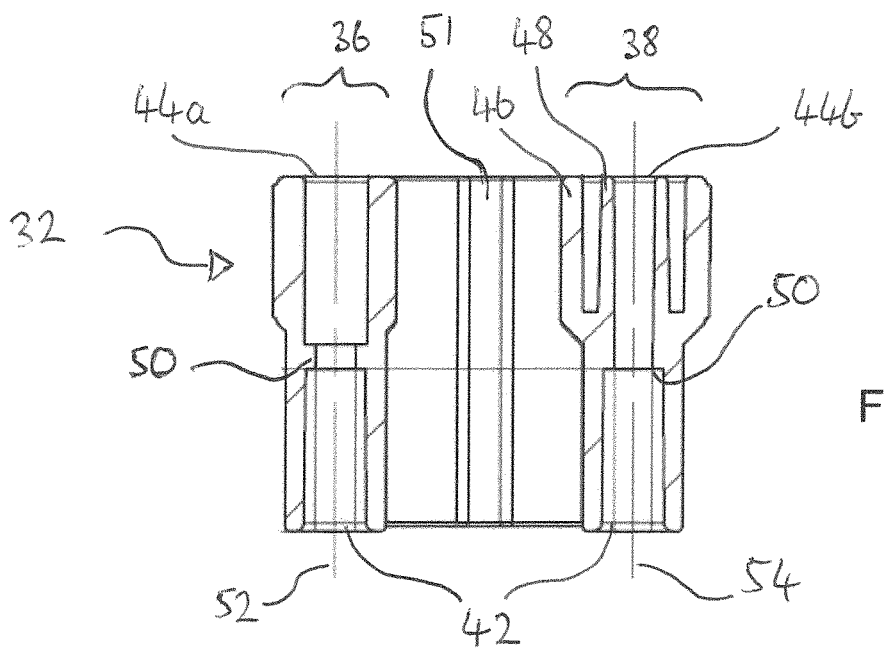
FIG. 5 is section view through the connector of FIG. 3 or 4.

The connector 32 is described in further detail with reference to FIGS. 3 and 5. The connector 32 comprises first 36 and second 38 connector formations and a bridge 40 there-between so as to couple the connector formations 36 and 38 together in a manner that allows the spacing between the connector formations to be varied in use. The connector 32, including the connector formations 36, 38 and the bridge 40, is conveniently formed as a unitary body or mass by a moulding process, such as injection moulding, and is preferably formed of a polymer material.

Each connector formation has a first opening 42, which in this example comprises an inlet opening. The inlet openings take the form of female connectors or recesses in which the ends of flow lines 22 and 24 are received with a close fit. The flow lines 22, 24 may be attached thereto by adhesive, such as a glue. The connector 32 and flow lines 22, 24 may thus form a secure assembly which is not intended to be separated in use. The opening 42 recesses may be substantially identical in form, i.e. having the same internal diameter and depth.

Each connector formation 36, 38 has a second opening 44 at the opposing side/end of the connector to the first openings 42. The second openings are different in width/diameter so as to form different connection formations for the different ports on the monitoring device 12. This helps to ensure the connector formations 36, 38 are not incorrectly attached to the monitoring device in use.

Opening 44a of connector formation 36 is a simple female connector, i.e. in the form of a recess which may be generally cylindrical or tapered in form. The external diameter of opening 44a is smaller than that of 44b but has a larger internal bore diameter.

The connector formation 38 has a pair of circumferential walls 46 and 48 surrounding opening 44b. The space between the walls 46 and 48 defines an annular recess around the central recess defined by the opening 44b and inner wall 48. The annular recess is thus of greater diameter than the central recess, which defines a bore and flow path through connector formation 38 in use. The annular recess terminates at an internal end wall, whereas the central recess passes right through the connector formation 38 to the opening 42.

Each of the connector formations 36 and 38 has an internal step or abutment formation 50 which limits the depth of the recesses in the connector body in which the tube ends and/or spigots are received in use.

The connectors formations 36 and 38 each extend in the direction of respective axes 52 and 54, which are substantially parallel so as to define straight flow paths through each connector formation.

The external surface of the connector formations 36 38 is textured towards the openings 44, for example by provision of ridges or similar formations in the external surface of the connector, e.g. so as to provide a grip portion. The external diameter of the connector formations 36, 38 is also greater towards openings 44 than towards openings 42 so as to provide a connector 'head' like form.

The bridge 40 comprises a shaped wall depending from each connector formation 36, 38 and spanning the gap therebetween. The wall thickness is such that the bridge can be deformed by pressing the connector formations 36, 38 together between a finger and thumb. The bridge 40 is shaped to provide portions 40a and 40b which are opposingly angled towards a generally central corner 51, which runs parallel with axes 52 and 54. The corner is rounded in this example, e.g. in the form of a hump or crease in the bridge material.

The bridge is of substantially uniform wall thickness in this example such that the form of the bridge promotes the required deformation in order to vary the spacing of the connector formations 36, 38 such that the connector is range-taking and can accommodate different spacing of ports on a monitoring device to which the connector is attached in use. The bridge is preferably resiliently deformable such that it is initially formed with a predetermined spacing between the connector formations 36, 38, which spacing will be maintained in the absence of external forces. When deformed the bridge will tend to return to, or towards, its original shape.

Figure 4:
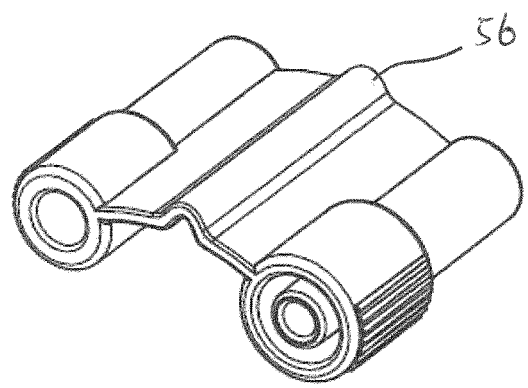
FIG. 4 is a three-dimensional view of a further example of a respiratory connector according to the invention.

Another example of bridge construction is shown in FIG. 4, in which the bridge 40 has an upstanding crease 56 substantially midway between the connector formations so as to provide a more defined hinge or corner portion about which the bridge will deform when the connector formations are pressed together. An acute angle may be formed in the crease 56, when in an undeformed, i.e. at-rest, condition whereas the remainder of the opposing bridge portions may display a reduced angle of offset. In any embodiment of the invention, adjacent portions of the bridge are preferably angled when in an undeformed condition, such that the internal angle between those adjacent portions is reduced by actuating the connector formations 36, 38.

Whilst the single piece, moulded construction of the connector 32 is considered beneficial in terms of its ease of manufacture, other embodiments could comprise a two-part hinge and/or biasing member, such as a spring, within the bridge if necessary.

Once connected in the manner described above and as shown in FIG. 1, the tubing product described above provides a continuous flow path between each of the adapter ports and the monitoring device ports in a manner that is simple to establish and easy to manage by an operator or carer.

Each of the connectors disclosed herein forms a friction connection with its respective port. Thus the connector formations and port formations/spigots are of corresponding shape and dimensions so as to form a tight fit, i.e. a so-called push-fit connection suitable for low pressure gas flow lines as used for respiratory systems of the kind described above.

Whilst connector inlets and outlets have been defined with respect to a particular mode of use of the connector and respiratory system, it will be appreciated that, in other embodiments or different types of spirometry apparatus, the inlet and/or outlet features of the connector flow passages may be reversed. The terms 'inlet' and 'outlet' used herein should be interpreted accordingly.

The invention claimed is:

1. A respiratory connector for connecting corresponding ends of a plurality of gas flow lines to a corresponding plurality of ports in use, the connector comprising:

a first connector formation comprising a first inlet opening, a first outlet opening and a first internal passage extending there-between;

a second connector formation comprising a second inlet opening, a second outlet opening and a second internal passage extending there-between; and a bridge extending between the first and second connector formations, wherein the bridge comprises a hinge and is actuable to allow a spacing between the first and second connector formations to be varied in use, the first connector formation, the second connector formation and the bridge are a single, unitary member, and the first connector formation and the second connector formation each have a length, the bridge extending from each of the first connector formation and the second connector formation along a majority of the length.

2. The respiratory connector of claim 1, wherein the bridge is resiliently deformable.

3. The respiratory connector of claim 2, wherein the bridge is formed of a resiliently deformable material and is arranged to flex upon actuation.

4. The respiratory connector of claim 1, wherein the hinge is defined by the bridge being arched or angled in form so as to deform when actuated to adjust the spacing between the first and second connector formations.

5. The respiratory connector of claim 1, wherein the bridge comprises adjoining bridge portions which are angularly offset when the bridge is in an unactuated condition.

6. The respiratory connector of claim 1, wherein the bridge takes the form of a wall having a wall thickness which is less than an internal passage dimension of the first and/or second internal passage.

7. The respiratory connector of claim 1, wherein the first and second inlet openings each comprise a recess adapted to receive respective first and second respiratory flow lines and the first and second outlet openings are each adapted to connect to flow monitoring ports of a respiratory flow monitoring device.

8. The respiratory connector of claim 1, wherein the first and second internal passages are parallel and linear in form, wherein the bridge is arranged to be deformable upon actuation about an axis which is parallel with the direction of the first and second internal passages.

9. The respiratory connector of claim 1, wherein the first and second inlets are the same in form but wherein the first and second outlets are different in form.

10. The respiratory connector of claim 9, wherein one of the first and second outlets comprises a plurality of concentric walls arranged to define an annular recess therebetween for connection to a port comprising a male spigot formation in use.

11. A respiratory tubing product comprising the respiratory connector of claim 1 and first and second flow lines depending from the first and second connector formations.

12. The respiratory tubing product of claim 11, wherein the first and second flow lines are connected together along a majority of their length.

13. The respiratory tubing product of claim 11, comprising a third flow line, the third flow line having a third connector formation that is separate from the respiratory connector.

14. The respiratory tubing product of claim 11, wherein the respiratory connector forms a distal end connector of the first and second flow lines, the product further comprising a proximal end connector attached to the opposing end of each of the first and second flow lines.

15. A respiratory tubing connector kit comprising the respiratory tubing product of claim 11 and an adapter for attachment in fluid communication with an inspiratory and/or expiratory gas flow path of a user breathing interface, the adapter comprising a main gas path and ports opening into said main gas path for communication with the first and second flow lines.

16. The respiratory connector of claim 1, wherein the single, unitary member is a unitary molded body of a polymer material.

17. The respiratory connector of claim 1, wherein the hinge is an upstanding crease midway between the first connector formation and the second connector formation.

\* \* \* \* \*